United States Patent [19]

Li

[11] Patent Number: 5,575,805
[45] Date of Patent: Nov. 19, 1996

[54] VARIABLE TIP-PRESSURE SURGICAL GRASPER

[75] Inventor: Lehmann K. Li, Milford, Conn.

[73] Assignee: Li Medical Technologies, Inc., Shelton, Conn.

[21] Appl. No.: 319,865

[22] Filed: Oct. 7, 1994

[51] Int. Cl.$^6$ .......................... A61B 17/32; A61B 17/28; A61B 17/42; A61B 17/44
[52] U.S. Cl. ............................. 606/206; 606/174
[58] Field of Search ................. 606/1, 205, 206, 606/207, 208, 174, 139–149, 167, 170; 433/159

[56] References Cited

U.S. PATENT DOCUMENTS

| | | | |
|---|---|---|---|
| 5,228,451 | 6/1993 | Bales et al. | 606/205 |
| 5,373,854 | 12/1994 | Kolozsi | 606/208 |
| 5,405,344 | 4/1995 | Williamson et al. | 606/205 |

*Primary Examiner*—Michael Powell Buiz
*Assistant Examiner*—Glenn Dawson
*Attorney, Agent, or Firm*—Pandiscio & Pandiscio

[57] ABSTRACT

A variable tip-pressure surgical grasper includes a shaft assembly, a jaw assembly, and a handle assembly. The jaw assembly is disposed adjacent to the distal end of the shaft assembly and has first and second movable jaws. Mandible portions of the jaws serve as the tissue manipulating portions and are arranged so that their distal tips engage without their proximal portions engaging. A slidable sleeve surrounds the shaft assembly and is movable between (i) a first retracted position wherein its distal end is spaced from the jaw assembly and (ii) a second extended position in which its distal end forces the jaw assembly closed. Instruments embodying the present invention may also include a ball joint coupling for coupling the jaw assembly to the shaft. The ball joint coupling allows the jaw assembly to be rotated about the axis of the shaft. The entire jaw assembly may also be of a modular construction so as to be fully detachable from the rest of the tool.

34 Claims, 17 Drawing Sheets

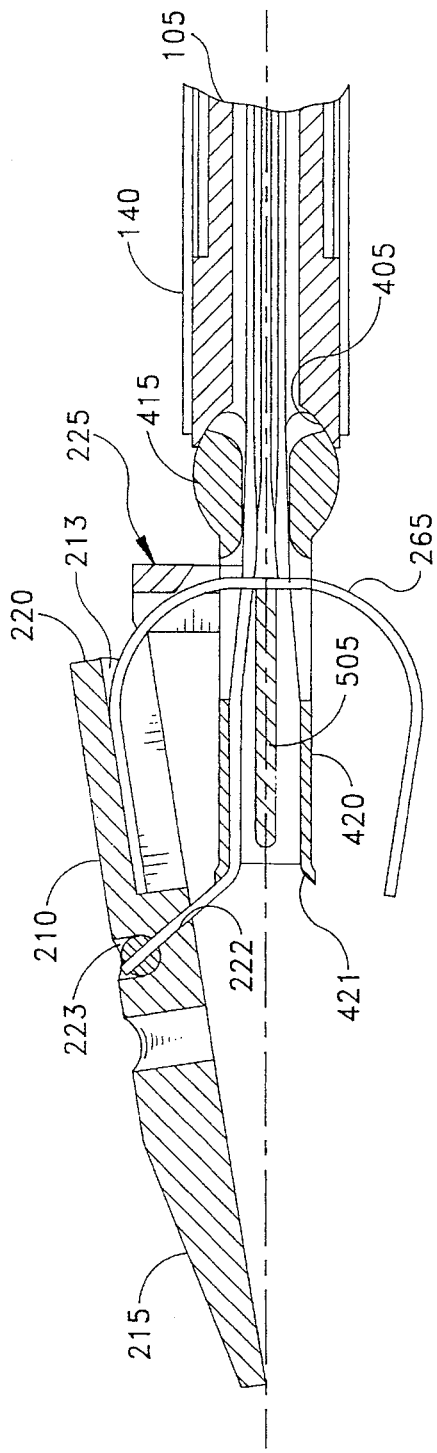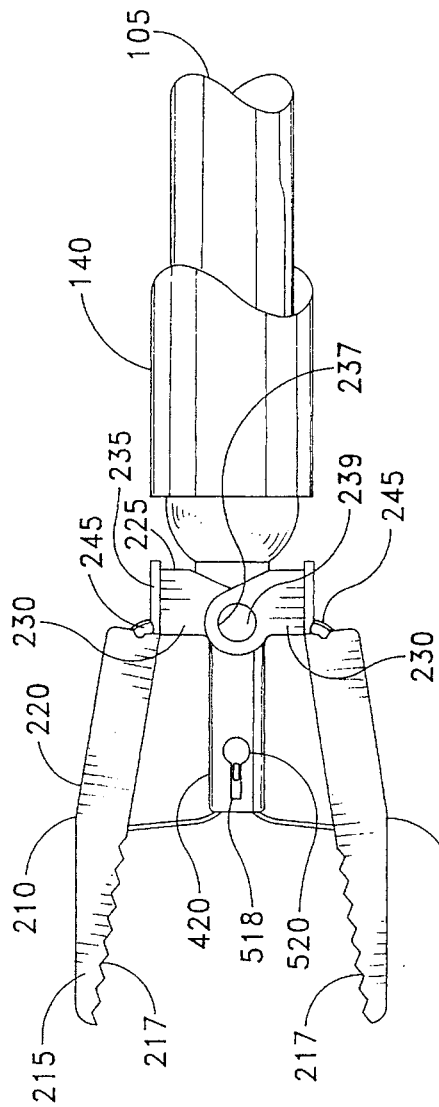

VARIABLE TIP-PRESSURE SURGICAL GRASPER

FIELD OF THE INVENTION

The present invention relates generally to surgical instruments, and more particularly to surgical instruments used to remotely grasp, cut, or otherwise manipulate bodily tissue.

BACKGROUND OF THE INVENTION

Endoscopic surgery often requires grasping or cutting bodily tissues and organs that are situated at some distance from the surgeon's hand. Various prior art linkages have been devised for converting a surgeon's manual efforts at the handle end of a surgical instrument into opening and closing of the instrument's jaws some distance away. Such prior art instrument's typically consist of a pair of articulated jaws, and a handle mechanism comprising two members, one movable with respect to the other, which can conveniently be manipulated so as to cause the jaws to open and close. Serrations, blades, or other features (depending upon the use for which the tool is intended) enable the jaws to perform various surgical functions, such as grasping or cutting. The articulated jaws are located at the distal end of a relatively long extension of the handle mechanism.

When operating the jaws of typical tools as described above, surgeons have experienced difficulty in grasping slippery tissues because the jaws close first at their rear ends and thereby tend to propel or push the tissues out from between the jaws. Consequently trauma of the tissues may result from repeated and increasingly aggressive attempts to grasp the tissue.

OBJECTS AND SUMMARY OF THE INVENTION

A primary object of the present invention is to provide an improved surgical grasper.

Another object of the present invention is to provide an improved surgical grasper having the capability of remotely altering the orientation of its jaws so that the axis of motion of the jaws is offset from the longitudinal axis of the shaft (i.e. a jaw assembly attached to the end of a shaft is angularly displaced with respect to the shaft's longitudinal axis).

Another object of the present invention is to provide a surgical grasper of the character described comprising tissue-manipulating jaws and manually-operated means remote from those jaws for causing the jaws to open and close in a predetermined manner.

A further object is to provide a surgical instrument of the type described which is characterized by a novel jaw assembly.

Still another object is to provide a surgical instrument of the type described above that has a detachable jaw assembly.

A further object is to provide a surgical instrument having a jaw assembly that can be swiveled about the longitudinal axis of the instrument.

These and other objects of the present invention are achieved through the provision and use of an instrument that preferably takes the form of a variable tip-pressure surgical grasper. The novel instrument of the present invention generally comprises a hollow shaft with a handle assembly attached to the proximal end of the shaft. The handle assembly comprises a body portion and at least one handle member movably mounted to the body portion so as to be capable of movement between first and second positions.

The instrument also includes a jaw assembly that is disposed adjacent to the distal end of the shaft. The jaw assembly comprises first and second movable jaws, with each jaw having a mandible portion with proximal and distal ends and a pivot portion connected to the proximal end of the mandible portion by hinge means, plus spring means for biasing the mandible portions away from one another. The mandible portions are disposed in confronting relation with one another and serve as the tissue manipulating portions of the jaw assembly. The instrument further includes means for pivotally connecting the pivot portions to one another and means for coupling the jaw assembly to the shaft. The jaw assembly is operated by means that include first and second cables that are disposed within the hollow shaft, with their distal ends being attached to the mandible portions of the two jaws. Anchor means are attached to the proximal ends of the cables and are mounted so as to be movable toward and away from the jaws. The anchor means is also coupled to jaw actuating means having at least one selectively movable actuating member for causing movement of the anchor means in a direction to exert tension on the cables. The points of attachment of the cables to the mandible portions of the jaws are such that application of tension to the cables by the jaw actuating means will cause the mandible portions to pivot on their hinge means so that the distal ends of the mandible portions of the jaws close on one another faster than their proximal ends. In a preferred embodiment, the jaw actuating means comprises two handle members for causing movement of the anchor means so as to exert tension on the cables.

In a preferred embodiment, a sleeve slidably surrounds the hollow shaft. The sleeve is movable between (i) a first retracted position wherein its distal end is spaced from the pivot portions of the jaw assembly and (ii) a second extended position in which its distal end forces the pivot portions to exert a force in a direction to cause the proximal ends of the mandible portions to engage one another.

Instruments embodying the present invention may also comprise a ball joint coupling for coupling the jaw assembly to the shaft. The ball joint coupling comprises a socket member on the distal end of the shaft and a ball-shaped member connected to the pivot portions of the two jaws. The ball-shaped member and the socket member are separable from one another to an extent that allows the jaw assembly to be rotated about the axis of the shaft. A selectively operable means is provided for pulling the ball-shaped member and the socket member into tight engagement with one another so as to lock the jaw assembly against rotation relative to the shaft.

In a further embodiment of the present invention, the entire jaw assembly may be of a modular construction so as to be fully detachable from the rest of the tool.

BRIEF DESCRIPTION OF THE DRAWINGS

These and other objects, features and advantages of the present invention will be more fully disclosed in, or rendered obvious by, the following detailed description of the preferred embodiments of the invention, which are to be considered together with the accompanying drawings wherein like numbers refer to like parts and further wherein:

FIG. 9 is a fragmentary longitudinal sectional view illustrating the relative positions of certain parts of one of the two jaws when the tips of the jaws are moved to grasping position;

FIG. 10 is a view like FIG. 8, showing the jaw assembly in its full open (release) position;

DETAILED DESCRIPTION OF THE PREFERRED EMBODIMENT

Referring first to FIGS. 1–13, the illustrated variable tip-pressure grasping device generally comprises a shaft assembly 100, a jaw assembly 200, and a handle assembly 300.

Figure 2:
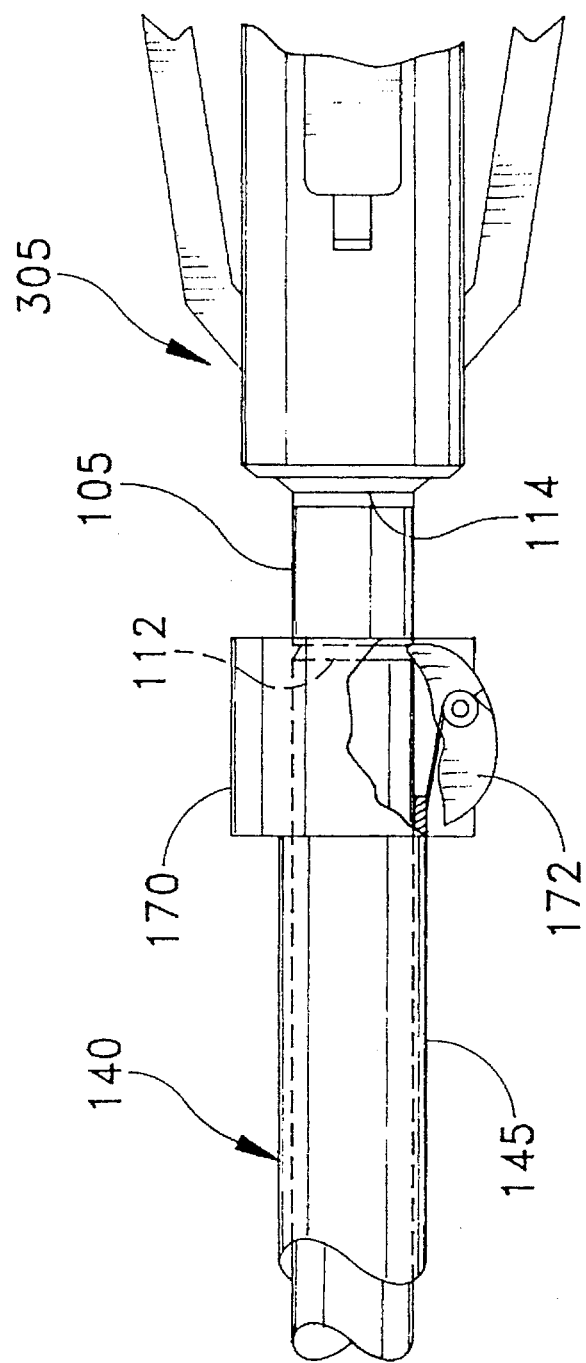
FIG. 2 is a fragmentary side elevational view, partially in phantom, with certain parts broken away, illustrating a spring latch assembly for the sleeve.
Figure 7:
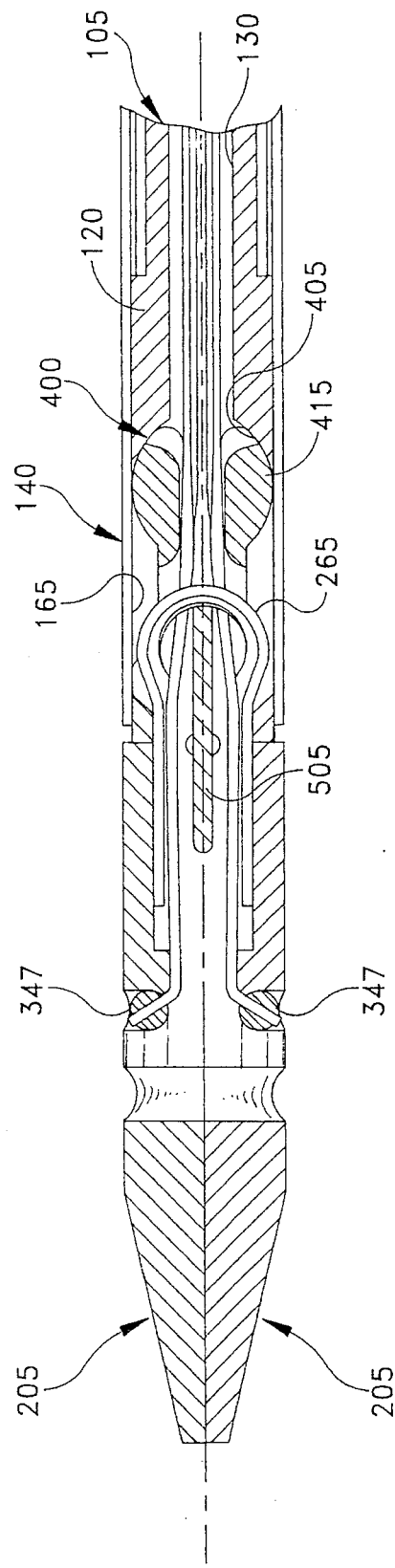
FIG. 7 is a longitudinal sectional view in elevation of the jaw assembly and distal portion of the sleeve and shaft when the jaw assembly is in its closed position.

As shown in FIGS. 2, 7, 9, 11 and 12, shaft assembly 100 comprises a shaft 105, and a sleeve 140 having a sleeve handle 170. Shaft 105 includes a proximal portion 110 (FIG. 2) and a distal portion 120 (FIG. 7). Proximal portion 110 also includes a pair of spaced-apart annular grooves 112 and 114 (FIG. 2). Shaft 105 is hollow, having a central passageway 130 that extends the full length of the shaft. Passageway 130 is sized so as to slidably receive at least two actuating cables, as will be hereinafter disclosed in further detail.

Figure 3:
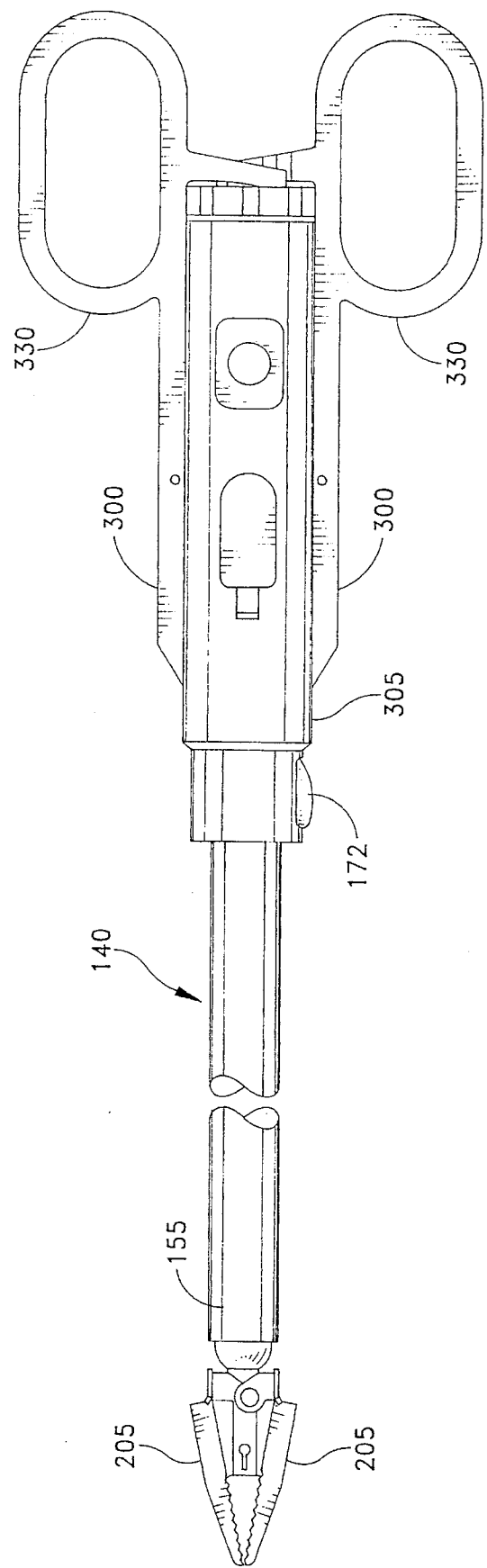
FIG. 3 is a side elevational view of the same instrument showing the jaw assembly in its "grasping position"
Figure 4:
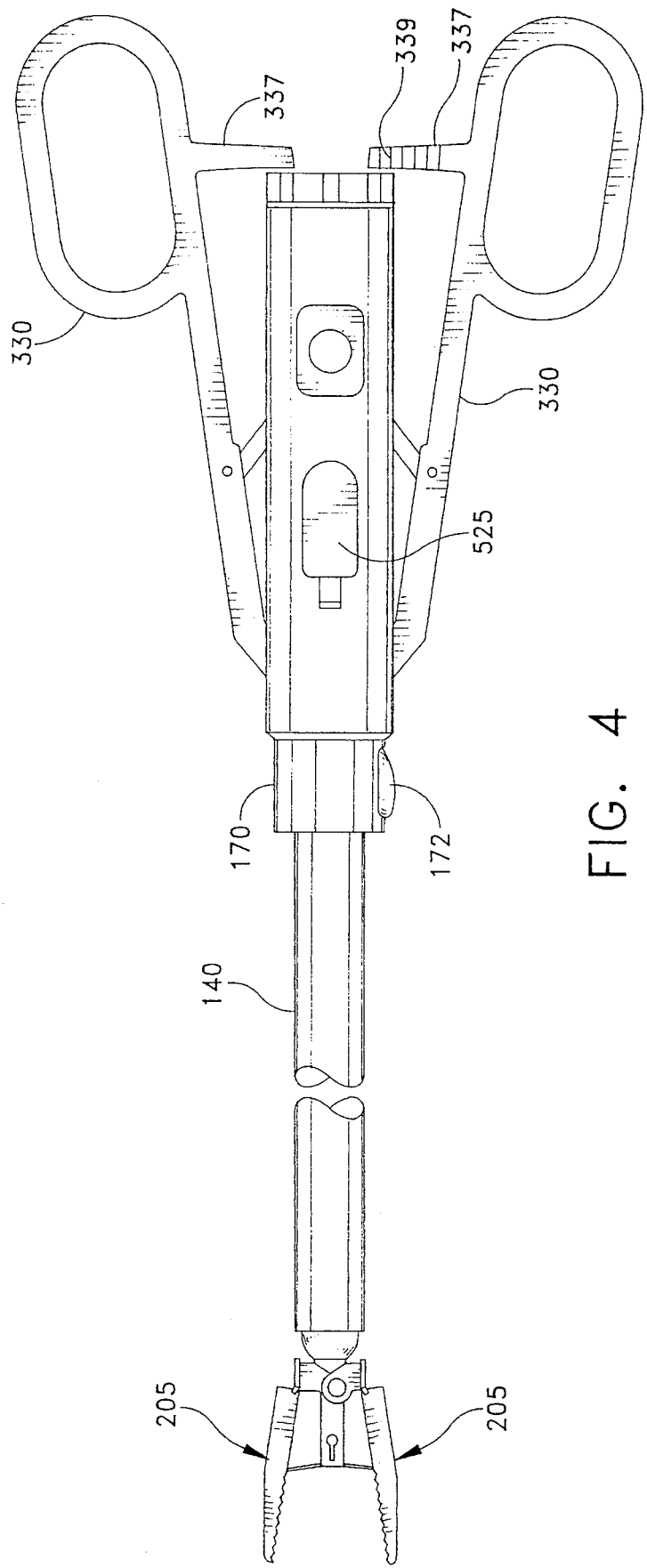
FIG. 4 is a side elevational view of the same instrument showing the jaw assembly in its fully open position.
Figure 5:
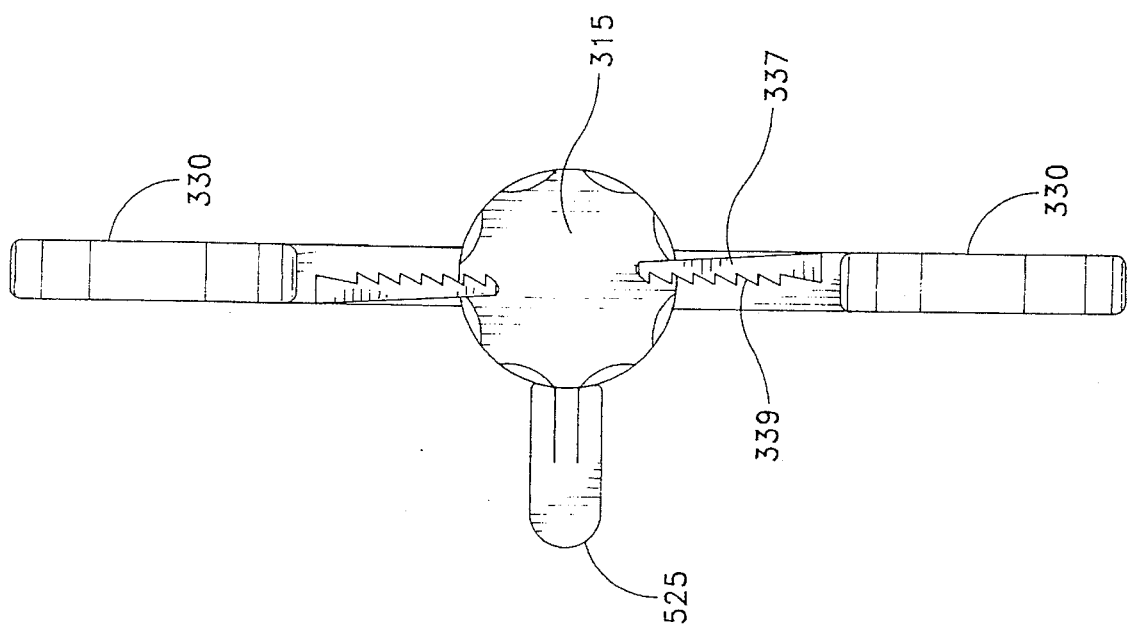
FIG. 5 is an elevational view of the rear end of the instrument shown in FIG. 4.
Figure 6:
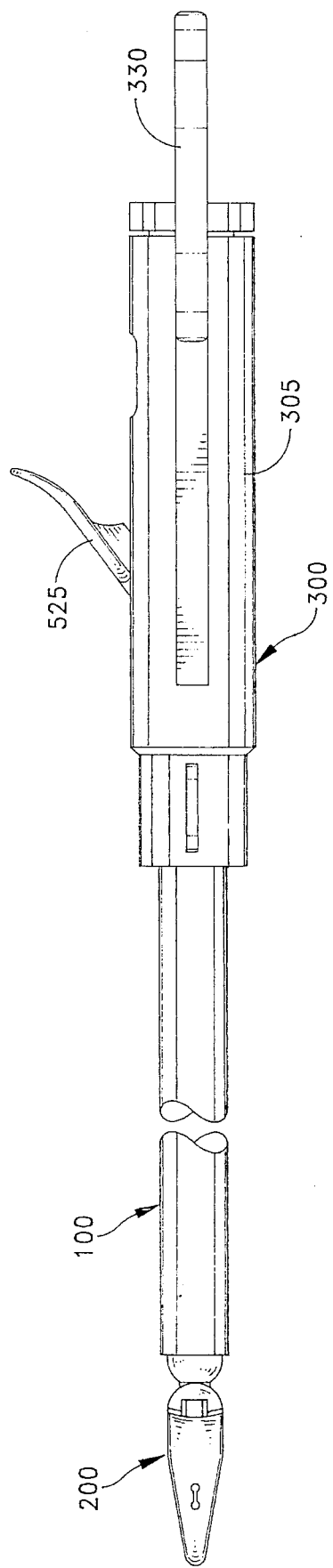
FIG. 6 is a plan view of the same instrument.

Sleeve 140 surrounds shaft 105 and includes a proximal portion 145 (FIG. 2) and a distal portion 155 (FIG. 3). The diameter of its inner surface 165 (FIG. 7) is sized so the sleeve makes a close sliding fit with shaft 105. In the preferred embodiment, sleeve 140 is shorter in length than shaft 105. Sleeve handle 170 is attached to the proximal portion 145. As seen in FIGS. 2-4, a spring-biased latch 172 is pivotally mounted to handle 170. The rear end of latch 172 is sized to make a locking fit in annular grooves 112 and 114, depending upon the position of sleeve 140 on shaft 105, as will be hereinafter disclosed in further detail. The latch is urged by its associated spring into locking engagement with grooves 112 and 114.

Referring now to FIGS. 1, 3, 4, 6 and 7–11, jaw assembly 200 comprises two jaws 205 and a spring 265. Each jaw 205 comprises a mandible 210, a pivot yoke 225, and a flexible hinge 245.

More particularly, and now referring to FIGS. 7–11, each mandible 210 comprises a distal or tip portion 215 whose inner surface is provided with serrations or teeth 217 to facilitate grasping an object, and a proximal portion 220 adapted to receive a portion of spring 265, as will hereinafter be disclosed in further detail. A bore 222 (FIGS. 7, 9, and 11) extends through mandible 210 at a point located between distal portion 215 and proximal portion 220, and the outer end of each bore is provided with a counterbore 223.

Each pivot yoke 225 comprises two mutually spaced pivot arms 230 and a bridge portion 235 that connects arms 230 at one end of those arms. The opposite ends of each pivot arm 230 has a pivot hole 237 that is sized so as to receive a pivot pin 239 that is used to attach the jaws as hereinafter described.

Mandibles 210 and pivot yokes 225 are coupled together by a flexible hinge 245. Hinge 245 may take various forms. Preferably it is a so-called "live" or "living" hinge that is formed integral with mandible 210 and yoke 225. Thus in the illustrated preferred embodiment, each jaw is molded of a tough yet flexible polymer, with hinge 245 being formed integral with mandible 210 and yoke 225. Alternately, mandible 210, yoke 225 and hinge 245 may be formed separately of the same or different materials, with the hinge thereafter being molded to the proximal end of the mandible and the bridge portion 235 of the yoke. In either case, hinge 245 comprises a relatively thin strip of flexible and resilient material that allows mandible 210 and pivot yoke 225 to swing (pivot) relative to one another.

Figure 11:
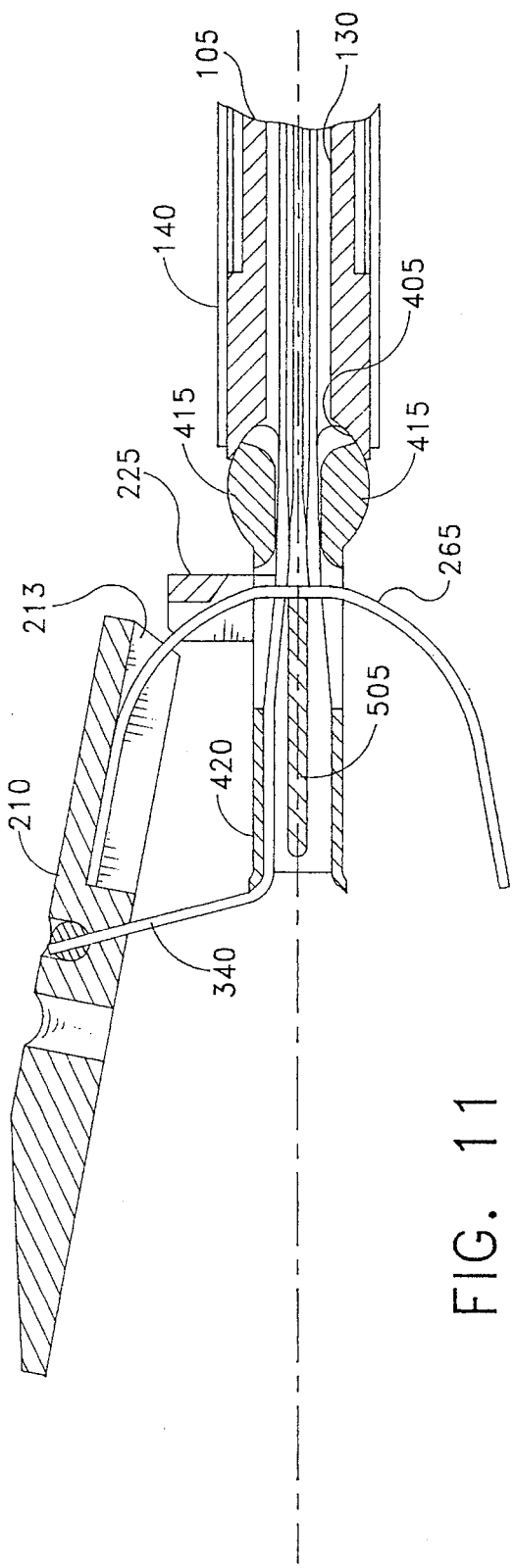
FIG. 11 is a fragmentary sectional view like FIG. 9, illustrating the relative positions of certain parts of one of the jaws when the jaw assembly is in its fully open or "release" position.
Figure 12:
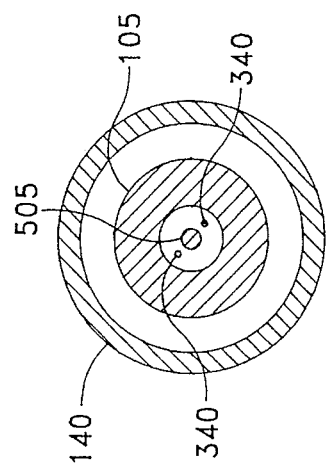
FIG. 12 is a cross-sectional view of the shaft assembly.
Figure 13:
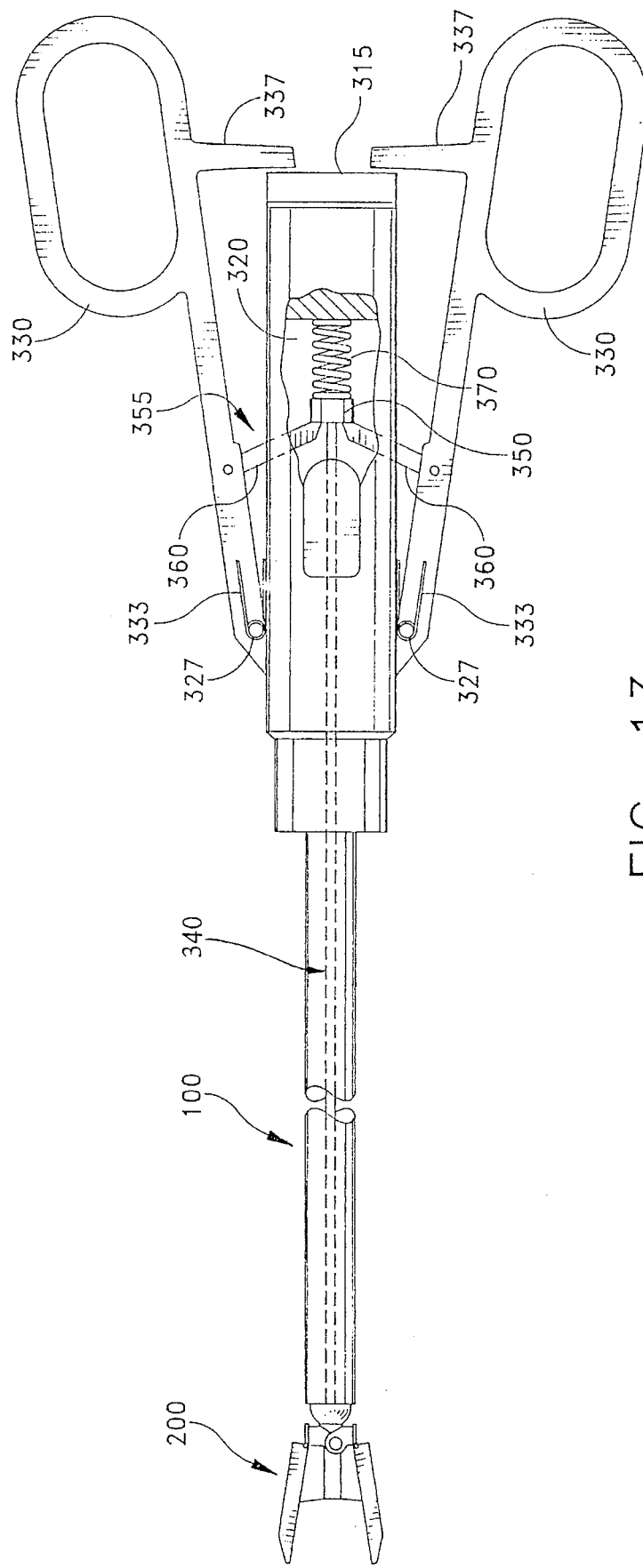
FIG. 13 is a side elevational view, partially in phantom, and partially broken away, showing the handle assembly and the mechanical linkage to the cables.

The inner surface of each mandible is recessed as shown at 213 (FIG. 9) to accommodate one end of a leaf spring 265. The spring acts on the confronting inner surfaces of the proximal portions 220 of mandibles 210 so as to bias the jaws outwardly to their open position (FIG. 11). Spring 265 must have sufficient resilience to withstand bending onto itself when jaws 205 are in their closed position, as shown in FIG. 7. Spring 265 may comprise a resilient metal such as carbon spring steel or one of the various titanium-nickel alloys well known in the art.

Referring now to FIGS. 3–6, and 8 and 13, handle assembly 300 comprises a body 305, a pair of handle members 330, two cables 340, an anchor block 350, and a mechanical linkage 355.

More particularly, and now referring to FIGS. 1, 3–6, 12 and 13, body 305 is elongate and further includes an internal passageway that is coextensive with the body, but is closed off at the proximal end of the body by a removable plug 315 so as to form a cavity 320 open at its distal end. The proximal portion 110 of shaft 105 is fastened to the distal (front) portion of body 305. The interior passageway of shaft 105 is aligned and communicates with cavity 320. In the preferred embodiment, body 310 is sized to easily accommodate a human hand. Handles 330 are pivotally fastened to body 305 by pivot pins 327.

Cables 340 are fastened at their proximal (rear) ends to anchor block 350 within cavity 320. Both cables extend from anchor block 350 through passageway 130 of shaft 105 to jaw assembly 200. The distal ends of cables 340 pass through a ball joint and a cable guide hereinafter described and into bores 222 of mandibles 210 (FIGS. 7, 9, and 11). The distal ends of the cables are anchored to the jaws by means of small balls 347 that are attached to the cables and make a tight fit in counterbores 223. If desired, balls 347 may be cemented in place in counterbores 223.

Mechanical linkage 355 comprises two levers 360, one for each handle member 330. Each lever 360 is pivotally fastened at one end to one of the handle members and at the other end to anchor block 350. A compression spring 370 is positioned between anchor block 350 and plug 315 of body 305 under compression, whereby it urges anchor block 350 toward the jaws, i.e., in a direction to reduce the tension in cables 340. Spring 370 also acts through levers 360 to urge the handle members to the open position shown in FIGS. 4 and 13. If desired, additional springs, e.g., coil springs 333 wrapped around handle member pivot pins 327 and having their opposite ends engaged with the handle members and body 305, may be used to assist spring 370 in urging the handle members to open position.

Referring now to FIGS. 7, 9, and 11, in the preferred embodiment, pivot yokes 225 are coupled to the distal portion of shaft 105 by a ball joint coupling 400. Ball joint coupling 400 comprises a hemispherically shaped socket 405 formed at the distal tip of shaft 105 and a ball-shaped member 415 which is formed on the proximal end of a hollow shaft 420. The latter functions as a cable guide and accordingly its forward end is flared as shown at 421 to assure easy movement of the cables. Ball-shaped member 415 has a hole that is aligned with the passageway defined by the inner surface of shaft 420. One end of that hole is bevelled as shown in FIG. 9 to reduce cable wear. Cables 340 extend through ball-shaped member 415 and shaft 420.

Ball-shaped member 415 is separable from socket 405 to an extent that allows jaw assembly 200 to be rotated about the longitudinal axis of shaft assembly 100. However, the instrument also includes selectively operable means for locking the jaw assembly against rotation relative to shaft 105. Such locking means comprises means for pulling the ball-shaped member and the socket member into tight engagement with one another so as to lock the jaw assembly against rotation relative to the shaft.

Figure 23:
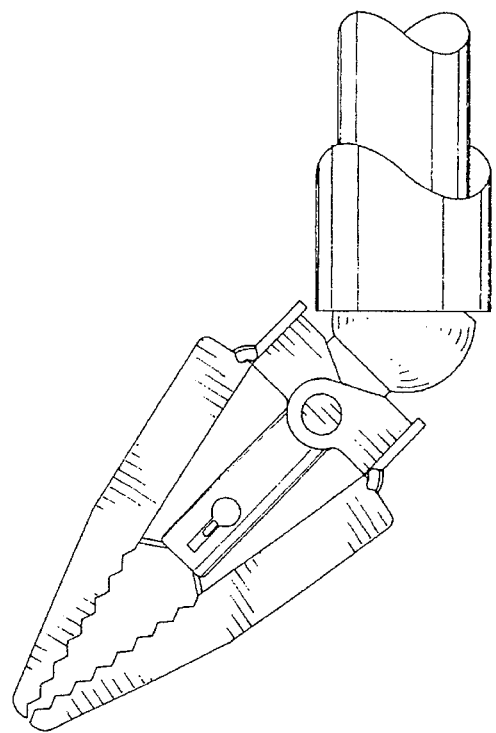
FIG. 23 is a side elevational view like FIG. 22, but with the jaw assembly in its tissue-grasping position.
Figure 22:
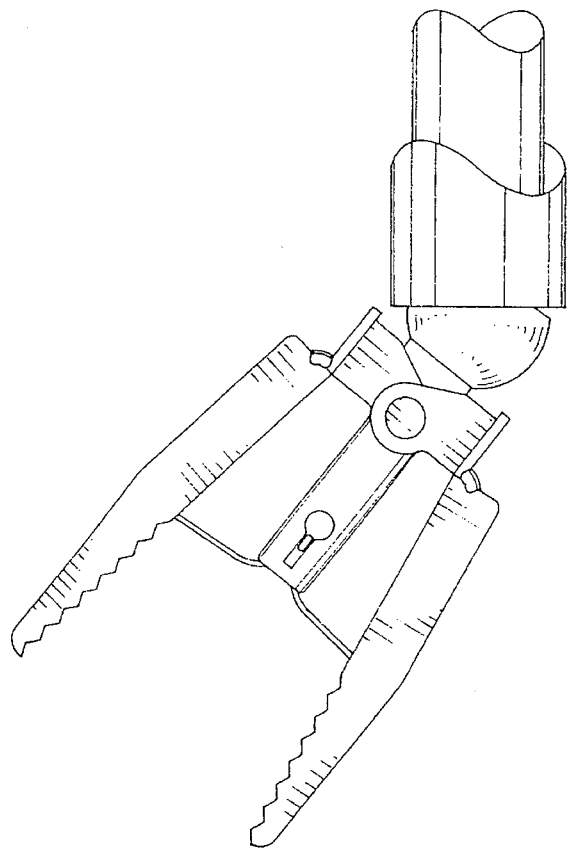
FIG. 22 is a side elevational view, partially broken away, showing the instrument of FIG. 3 with its jaw assembly adjusted at an angle to the longitudinal axis of the shaft assembly, with the jaws in open position.
Figure 24:
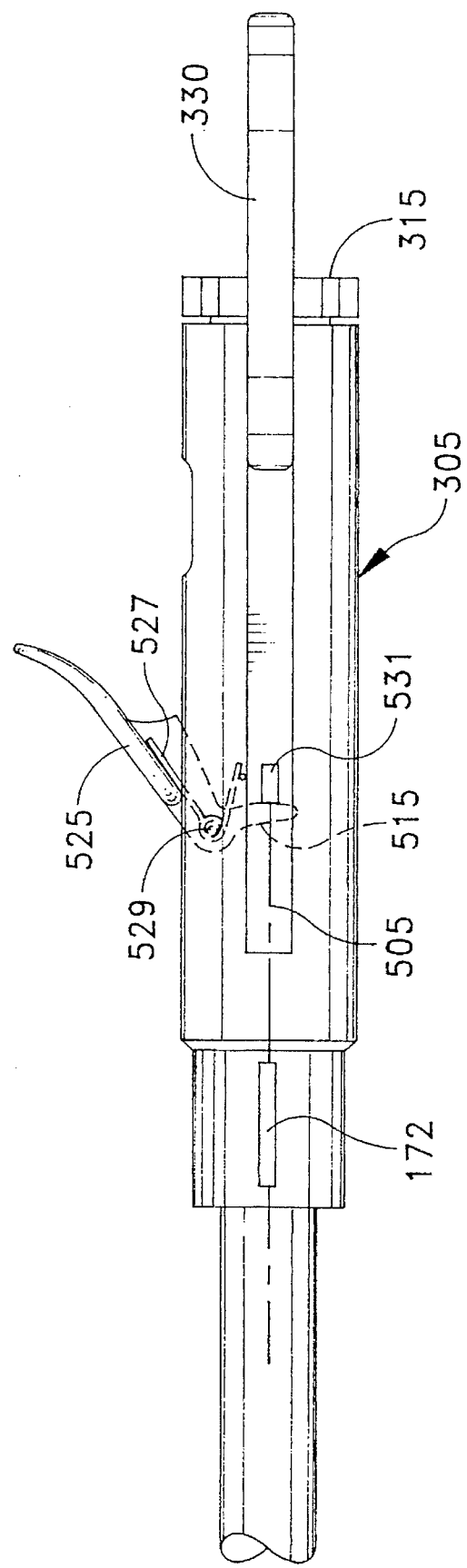
FIG. 24 is a fragmentary plan view of the handle assembly illustrating details of showing the release lever mechanism for the ball joint connection.

More specifically and with reference to FIGS. 1–7, 9, 11, and 24, the selectively operable locking means comprises a release/lock cable 505 and a release/lock lever 525. Cable 505 extends through the center hole in ball-shaped member 415 into shaft 420 and its distal end extends through a side opening 518 and terminates in a ball-shaped anchor 520 that is larger than the side opening and bears against the outer surface of the shaft. As seen best in FIGS. 1, 3, 4, 6, and 24, release/lock lever 525 is pivotally mounted to body 305 of the handle assembly. A leaf spring 527 biases release/lock lever 525 in a counterclockwise direction (as seen in FIG. 24) about its pivot pin 529. The inner end 515 of lever 525 is bifurcated so as to straddle cable 505. That bifurcated end is engaged with an anchor block 531 that is disposed adjacent to anchor block 350 in cavity 320. However, anchor block 531 is displaced laterally of anchor block 350 so as to avoid interference with cables 340. The bias exerted by spring 527 causes lever 525 to force anchor block 531 away from the jaw assembly, thereby drawing ball-shaped member 415 into tight engagement with socket 405 so as to lock the jaw assembly against rotation. When it is desired to rotate the jaw assembly to an angulated position as shown in FIGS. 22 and 23, lever 525 is depressed, thus reducing the tension in cable 505 and releasing the jaw assembly enough to permit it to be swivelled at its ball joint. Then lever 525 is released so as to cause cable 505 to again pull the ball 415 tight against socket 405.

Operation of the instrument of FIGS. 1–13 will now be described.

Figure 1:
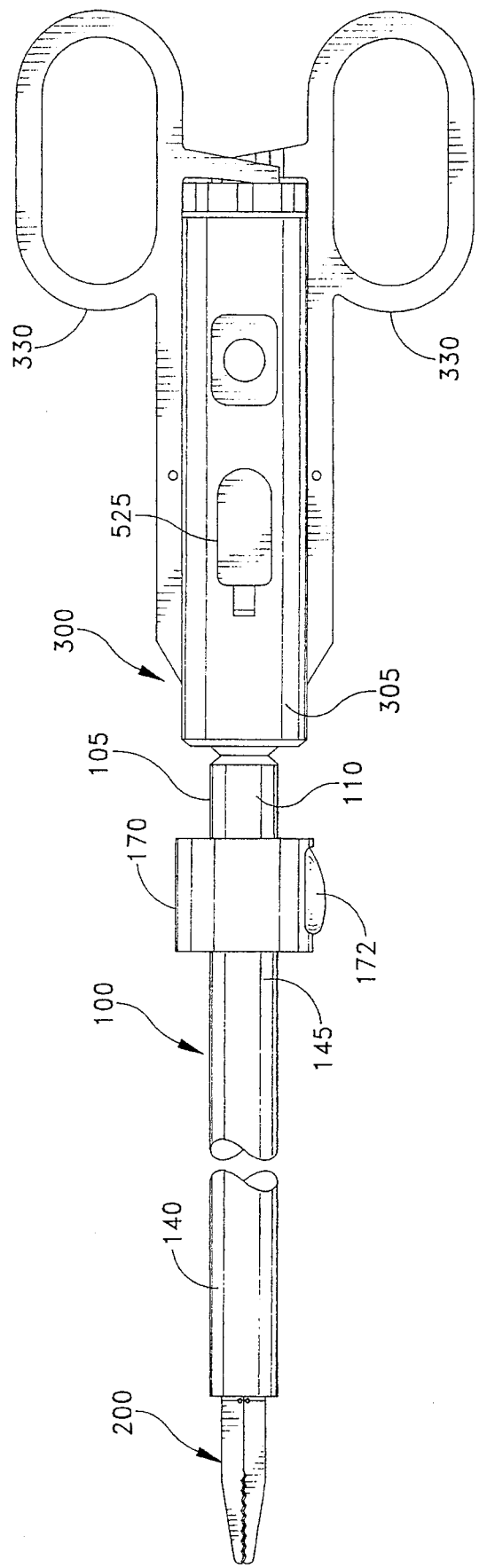
FIG. 1 is a side elevational view of a grasping device constituting a preferred embodiment of the present invention.

Referring to FIGS. 1–4, 7, 13, and 24, to place jaw assembly 200 near to a surgical site, handle members 330 are first moved to their closed position against body 305 (FIG. 1), thereby moving the jaws to the position shown in FIG. 3, and then sleeve 140 is moved to its distal (forward) position relative to shaft 105, thereby causing the sleeve to force jaws 205 to their fully "closed" position (FIGS. 1 and 7), wherein the proximal portions 220 of mandibles 210 are positioned with their tissue-engaging surfaces being parallel to and engaging or nearly engaging one another, and spring 265 being fully compressed between them. At this point latch 172 coacts with groove 112 to lock the sleeve against rearward movement relative to shaft 105. When sleeve 140 is moved to its forward position, it engages pivot yokes 225 and rotates them about pins 239 so as to bring bridge portions 235 into contact with shaft extension 420. In this closed position the distal (forward) end portion of sleeve 140 overlies pivot arms 230 of pivot yokes 225, thereby maintaining jaw assembly 200 in its fully closed configuration (FIGS. 1 and 7). With jaws 265 held in their fully closed position by sleeve 140, the forward end of the instrument presents its smallest possible cross-sectional profile, thus facilitating its insertion via a cannula into a patient's body via a suitable incision (e.g.) an incision through the abdominal wall of a surgery patient. Once the forward end of the grasper is clear of the cannula, the surgeon may open the jaws for the purpose of grasping tissue at the surgical site. To "open" jaw assembly 200, the operator depresses latch 172 to unlock sleeve 140, and then uses sleeve handle 170 to move the sleeve rearwardly until latch 172 engages annular groove 114 to lock the sleeve in its rear position. When this is done, the front end of sleeve 140 is located rearwardly of jaw assembly 200, exposing pivot yokes 225 and thereby freeing the jaws for opening movement. As soon as sleeve 140 clears and thus exposes pivot yokes 225, spring 265 causes the proximal ends of mandibles 210 and pivot arms 230 to rotate outwardly, away from shaft extension 420. As this outward movement occurs, the distal ends of mandibles 210 remain in closely spaced relation with one another, thus yielding the jaw position shown in FIGS. 3 and 8.

However, before the surgeon can grasp an object, jaw assembly 200 must be placed in the fully open position shown in FIGS. 4 and 10. This is accomplished by moving handles 330 from their closed position adjacent to body 305 (FIG. 2) to their open position spread outwardly of body 305 (FIG. 4). As handles 330 are pivoted outwardly away from body 305 (FIG. 4), levers 360 cause anchor block 350 to move distally, relieving the tension in cables 340. This in turn results in the distal (tip) portions 215 of mandibles 210 separating automatically under the force exerted by spring 265.

Figure 8:
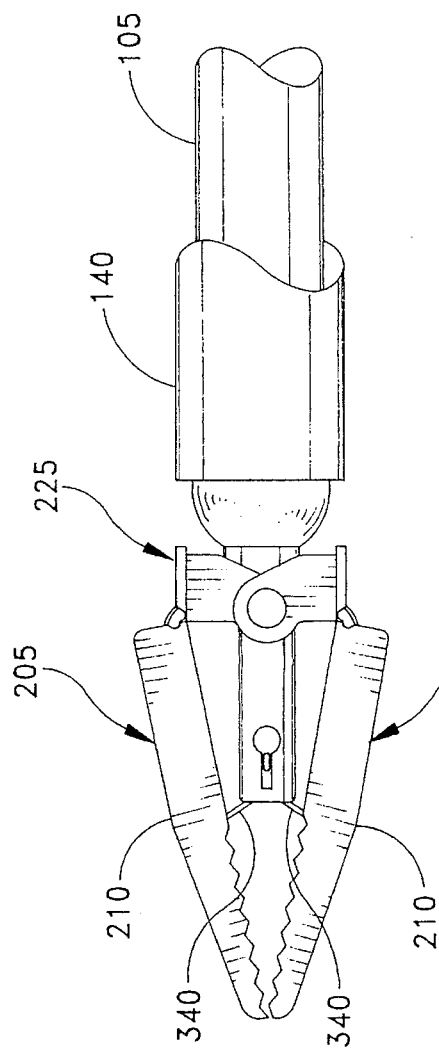
FIG. 8 is a fragmentary side elevational view of the jaw assembly on an enlarged scale, showing how the tips of the jaws are engaged first when the jaws are moved to grasping positions.

The open jaw assembly 200 is then moved into position around a target (tissue or other object at the surgical site). Once jaws 205 are in place around the target, handles 330 are squeezed together. This action causes levers 360 to move anchor block 350 rearwardly away from the jaws, thereby driving cables 340 in the same direction. As a consequence, cables 340 pull the distal portions 215 of mandibles 210 together in a tissue-grasping position, but the proximal portions of the jaws remain separated as shown (FIGS. 3, 8, 9). Of course, the object may be released by simply moving handles 330 back to their above-described open position.

Removal of the instrument from the surgical site involves opening the handle members to release the grasped object, then closing the handle members to restore the jaws to position of FIG. 8, then moving sleeve 140 forward to cause the rear ends of the jaws to shift to the position of FIG. 1, and then withdrawing the instrument from the patient.

Although not necessary, it is preferred to provide handle members with locking means for locking those members in a selected closed position. As shown in FIGS. 1, 3, and 4, handle members 330 may be provided with resilient tangs 337 having a length such that they overlap as the handle members are moved from the open position of FIG. 4 to the closed position of FIGS. 1 and 3. The inner mutually confronting surfaces of the tangs have teeth 339 that coact to lock the handles in different positions. Tangs 337 allow the handles to be locked at various jaw-closing positions, whereby to assure grasping of tissue or other objects at different grasping force levels.

Jaw assembly 200 may be swivelled about the longitudinal axis of shaft assembly 100 in the following manner. Release/lock lever 525 is depressed sufficiently to relieve the tension in release/lock cable 505 so as to cause socket member 405 and ball-shaped member 415 to slightly separate from one another. In this way, ball-shaped member 415 is free to swivel relative to socket member 405. Another instrument is inserted into the patient and then urged against jaw assembly 200 so as to force ball-shaped member 415 to swivel into the desired position. The release/lock lever 525 is then released, whereupon spring 527 forces lever 525 to exert a pulling force on cable 505, with the result that ball-shaped member 415 and socket member 405 are moved into tight engagement with one another, effectively locking jaw assembly 200 against further movement relative to shaft 105.

Figure 25:
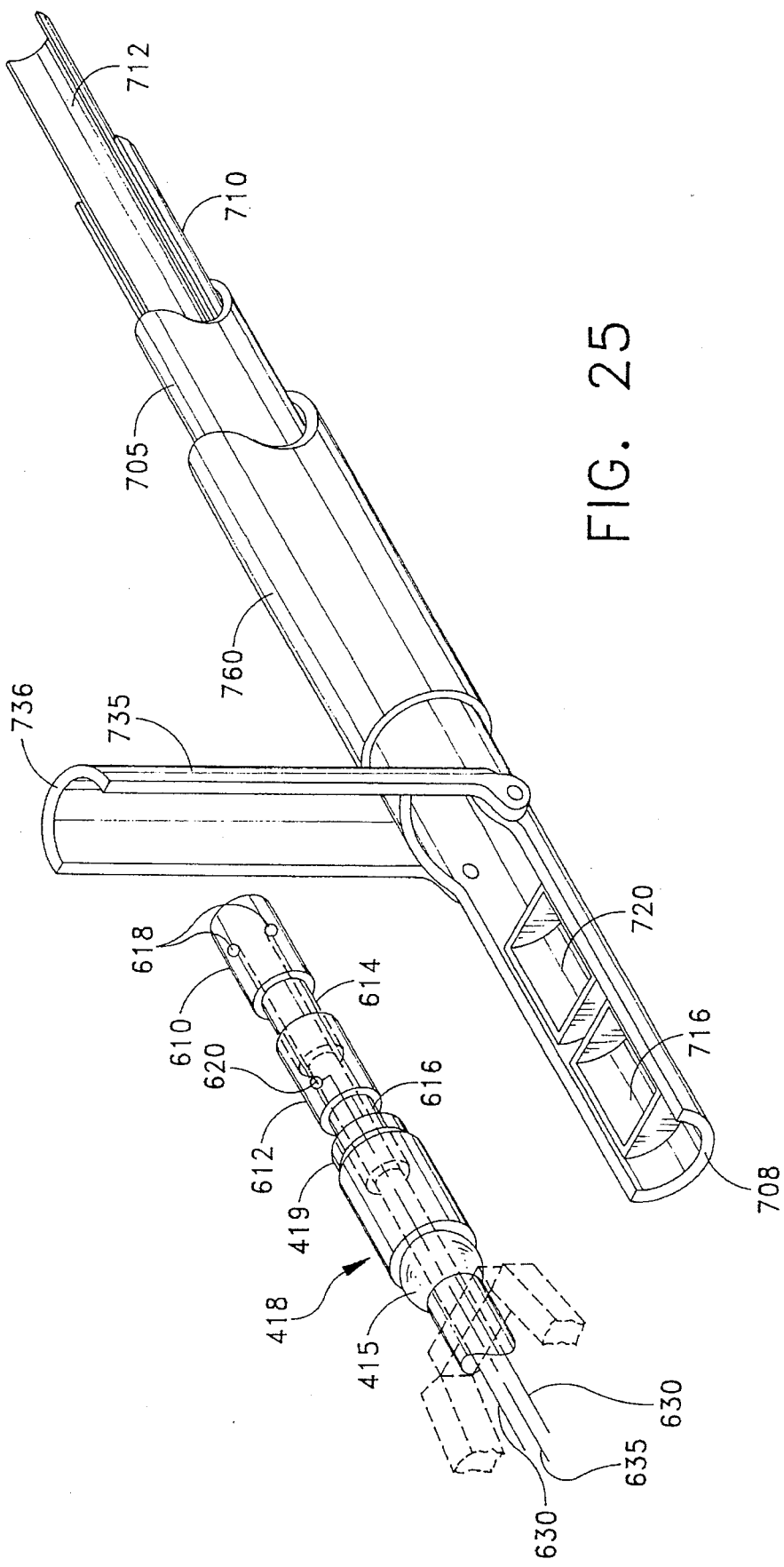
FIG. 25 is a fragmentary exploded perspective view of an alternative embodiment of the invention having a detachable jaw assembly.

In an alternative embodiment of the present invention, a detachable jaw module 600 may replace jaw assembly 200, as seen in FIG. 25. Detachable module 600 comprises two cable anchors in the form of hollow cylinders 610 and 612, two mandible cables 630, a release/lock cable 635, a ball joint coupling 400, and a jaw assembly 200. Cable anchor 610 has a reduced diameter hollow cylindrical extension 614, and cable anchor 612 has a similar reduced diameter hollow cylindrical extension 616. Extension 614 makes a close sliding fit inside of anchor 612, while extension 616 makes a close sliding fit inside of a socket tube 418. The latter has a hemi-spherically shaped socket in its front (distal) end to accommodate the ball 415 of a cable guide like the one shown in FIGS. 8-11. Tube 418 has a circumferential groove 419 adjacent its proximal (rear) end. Cable anchor 610 has two side bores 618 and the proximal ends of cables 630 are secured in those holes. Cable anchor 612 has a single side bore 620 in which the proximal end of cable 635 is secured. Although not shown, the opposite ends of cables 630 and 635 extend through the center hole of ball 415 and the extension 420 of the cable guide and are anchored in the mandible portions of a jaw assembly like the one shown in FIGS. 7, 9 and 11.

Further with respect to the instrument shown in FIG. 25, it includes a modified shaft assembly 700 that comprises a hollow shaft 705 that is fixed at its proximal end to a handle assembly like the one previously described. The distal (front) end portion of shaft 705 is cut away so as to constitute essentially a half cylinder, as shown. That half cylinder portion of shaft 705 is provided with a semi-cylindrical end flange 708 that is sized to fit in groove 419 of socket tube 418. Slidably disposed in shaft 705 are first and second slides 710 and 712, with slide 710 engaging shaft 705 and slide 712 engaging slide 710. The forward end of slide 710 has two partitions that together form a pod 716 that is sized to accept anchor 612. The forward end of slide 712 has two partitions that together form a pod 720 that is sized to accept anchor 610. The rear ends of slides 710 and 712 are connected to mechanisms (not shown) similar to those described above that include handle members 330 and release lever 525. Additionally a semi-cylindrical cover member 735 is pivotally attached to the distal end of shaft 705. That cover member has a semi-cyclindrical end flange 736 that complements flange 708. The inner diameters of flanges 708 and 736 are such that the flanges make a close fit in groove 419.

The modular shaft assembly also includes a sleeve 760 that is essentially like and serves the same function as sleeve 140.

The modular jaw assembly is attached to the modified shaft assembly 700 by lifting cover member 735 up to the inclined position shown in FIG. 25, placing the section of the socket tube containing groove 419 in line with flange 708 and placing anchors 610 and 612 in pods 720 and 716 respectively. Thereafter the cover is closed so that flange 736 also goes into groove 419, thereby locking the modular jaw assembly to the modified shaft assembly. Thereafter the jaw assembly is operated in the same way described for the preferred embodiment, with manipulation of the two handle members corresponding to members 330 causing slide 710 to move axially and thereby alter the tension on cables 630, and manipulation of the release member attached to cable 635 causing slide 712 to move axially to release ball member 415 from tight engagement with the socket tube, whereby to permit the jaw assembly to be pivoted as described above.

In light of the foregoing, various changes, modifications, and additions will become obvious to those persons skilled in the art and are, therefore, believed to fall within the scope of the present invention.

Figure 16:
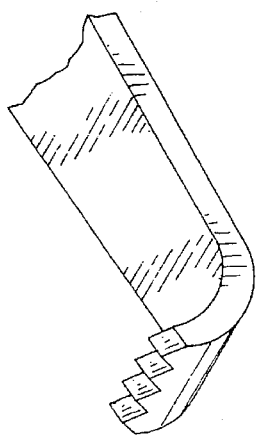
FIGS. 15–18 illustrate still other alternative mandible forms that may be incorporated in the present invention.
Figure 18:
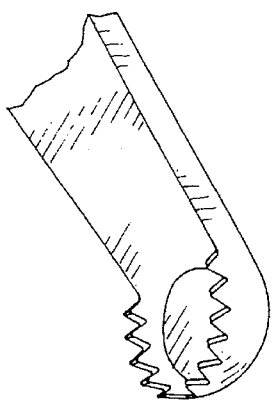
Figure 15:
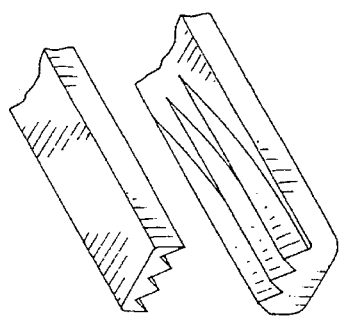
Figure 17:
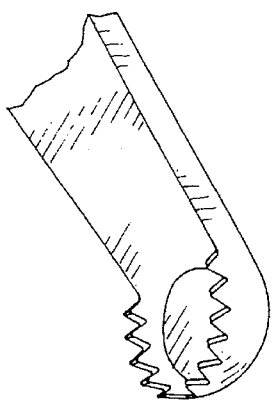
Figure 14:
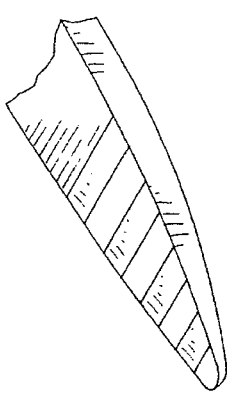
FIG. 14 illustrates an alternative form of mandible grasping surface.
Figure 19:
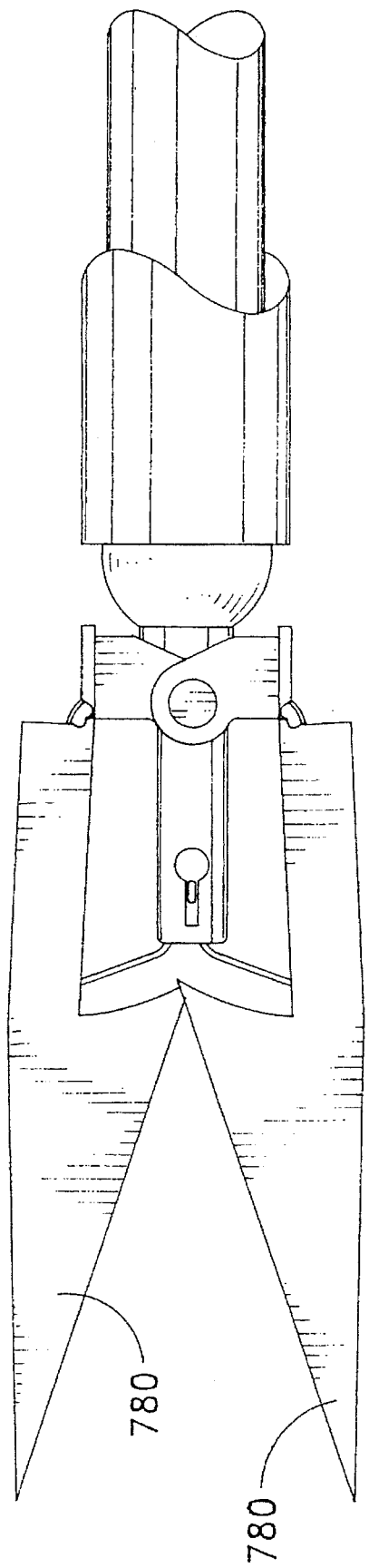
FIG. 19 is a side elevational view of shearing-type jaw assembly.

For example, FIGS. 14–18 illustrate a variety of grasping surfaces contemplated for use with the present invention. FIG. 14 represents a standard smooth surface mandible. FIG. 15 illustrates a DeBakey style grasper having both fine and coarse teeth. FIGS. 16, 17, and 18 respectively show Martin's, Standard tooth, and Russian style graspers. Shears-type jaws having sharp shearing edges as shown at 780 in FIG. 19 may also be used with the present invention. Of course, other forms, styles, and arrangements of teeth and grasping means will be obvious to those skilled in the art.

Figure 20:
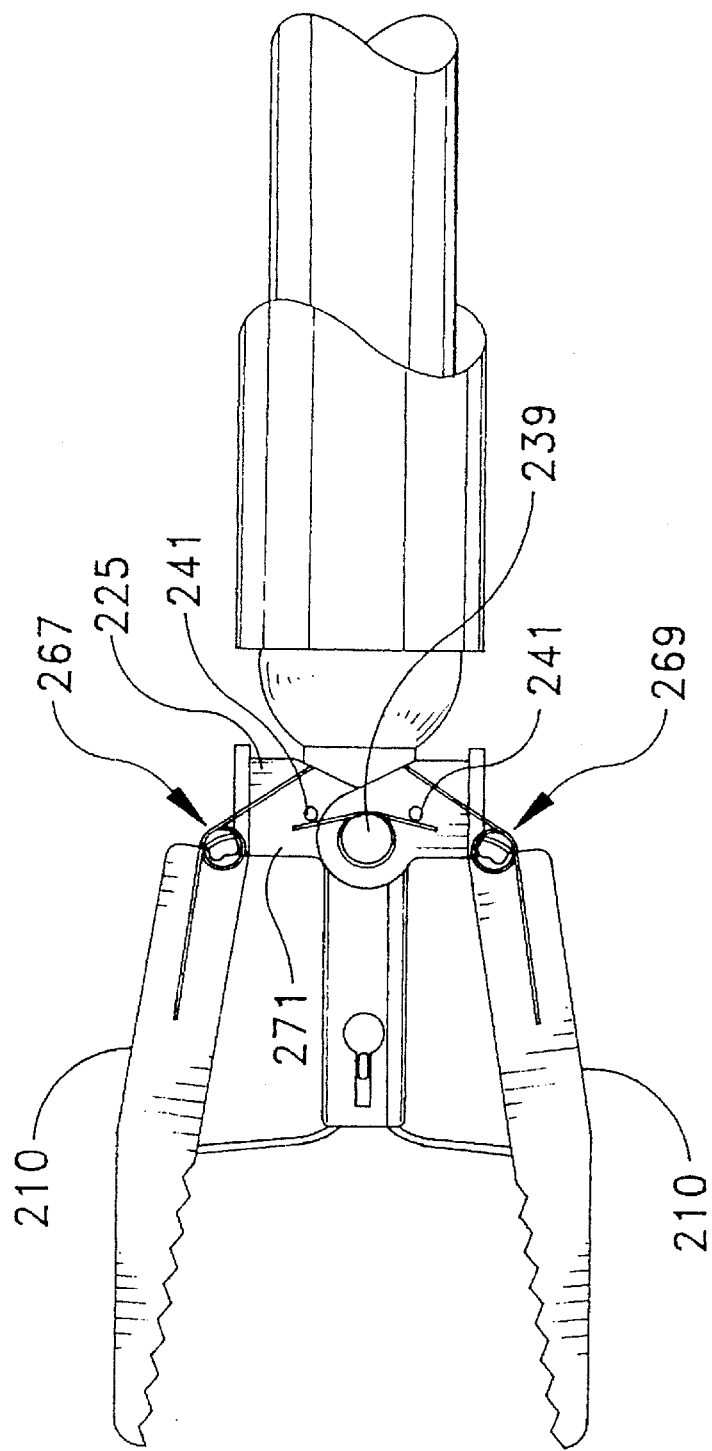
FIG. 20 is a side sectional view of an alternative form of jaw assembly utilizing multiple springs.

Another alternative form of jaw assembly is shown in FIG. 20 comprising three straight torsion springs 267, 269 and 271 in place of leaf spring 265. Springs 267 and 269 are positioned over lateral extensions of flexible hinges 245, with one of their ends locked in a recess in mandible 210 and the other end locked in a recess in a pivot yoke 225. The third spring 271 is positioned over pivot pin 239, with its opposite ends bearing against pins 241 anchored in pivot yoke 225. Springs 267 and 269 act to urge the two mandibles to fully open position, while spring 271 urges the two pivot yokes to rotate away from the jaw tips so as to keep them in the position shown in FIG. 20.

Figure 21:
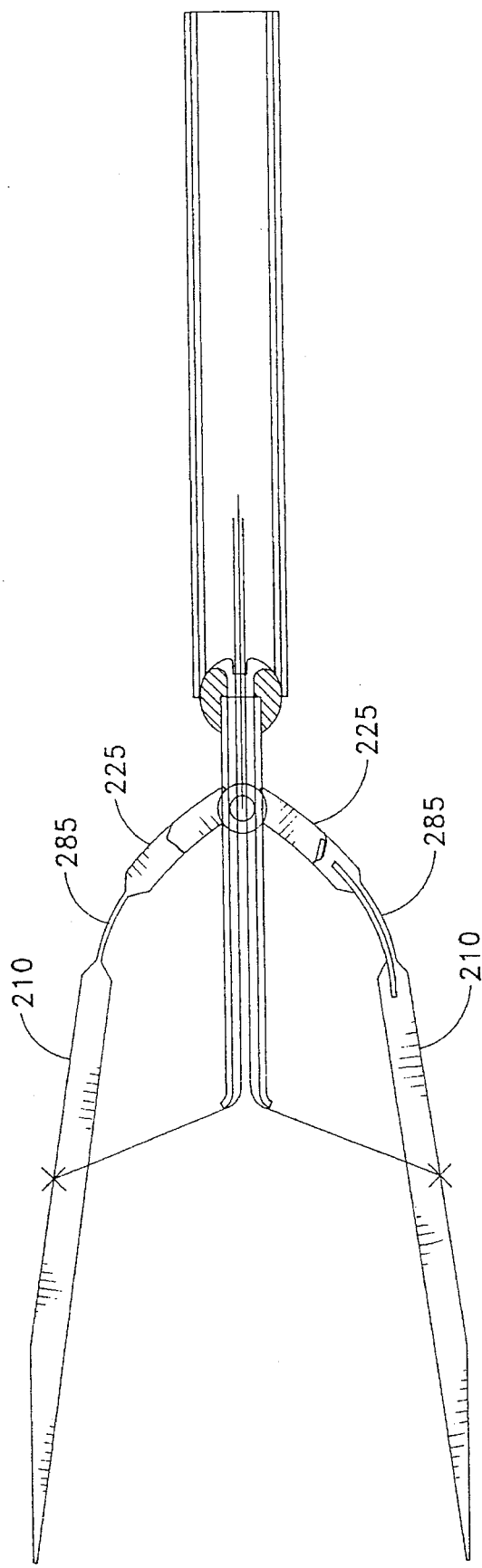
FIG. 21 is a fragmentary side elevational view, partially in section, showing an alternative form of jaw assembly comprising a metal hinge.

In a further example, seen in FIG. 21, mandibles 210 and yokes 225 are fastened together by a metal hinge 285. In this embodiment, mandibles 210 and yokes 225 may be formed separately from the same or different materials. Hinge 285 may either be insert-molded or otherwise fastened to the proximal end of mandible 210 and bridge portion 235 of yoke 225. In either case, hinge 285 comprises a relatively thin strip of flexible and resilient metal that allows mandible 210 and pivot yoke 225 to swing (pivot) relative to one another.

Of course, it will be understood that jaw assembly 200 may be fastened directly to distal portion 120 of shaft 105 without the need for a ball joint coupling.

Another obvious modification is to eliminate the ball joint entirely and instead secure the guide tube 420 directly to the distal end of shaft 105. It also is contemplated that two springs 265 may be used, with the two springs straddling cables 340 and 505. Still other changes will be obvious to persons skilled in the art.

What is claimed is:

1. A surgical grasper comprising:

a hollow shaft having a distal end and a proximal end;

a handle assembly connected to the proximal end of said shaft, said handle comprising a body portion and at least one handle member movably mounted to said body portion so as to be capable of movement between first and second positions;

a jaw assembly adjacent the distal end of said shaft, said jaw assembly comprising first and second movable jaws with each jaw having a mandible portion with proximal and distal ends and a pivot portion connected to the proximal end of said mandible portion by hinge means, each of said pivot portions being in the form of a yoke having a bridge section connecting two side arm sections, and further wherein said pivot portions are pivotally coupled together by a pivot pin that extends through said side arm sections, said mandible portions being disposed in confronting relation with one another, said jaw assembly further including means for pivotally connecting said pivot portions to one another and coupling said jaw assembly to said shaft, and first spring means for biasing said mandible portions away from one another;

first and second cables having proximal and distal ends with said distal ends attached to the mandible portions of said first and second jaws respectively;

anchor means attached to said proximal ends of said cables, said anchor means being mounted so as to be movable toward and away from said jaws; and jaw actuating means coupled to said anchor means for causing movement of said anchor means in a direction to exert tension on said cables and thereby cause only the distal ends of said mandible portions of said jaws to close in response to movement of said at least one handle member relative to said body portion.

2. A grasper according to claim 1 further including second spring means for urging said anchor means in a direction to relieve the amount of tension exerted on said cables, whereby to permit said jaws to open under the action of said first spring means.

3. A grasper according to claim 1 wherein said first spring means consists of a single leaf spring that is bowed and has its opposite ends engaged with said mandible portions of said jaws.

4. A grasper according to claim 1 wherein said jaw actuating means comprises a mechanical linkage between said at least one handle member and said anchor means, whereby movement of said at least one handle member will cause movement of said anchor means to vary the tension on said first and second cables.

5. A grasper according to claim 1 wherein said hinge means are formed integral with said jaws and said pivot portions.

6. A grasper according to claim 5 wherein said jaws, said pivot portions and said hinge means are made of a plastic material.

7. A grasper according to claim 1 wherein said distal ends of said cables are connected to said mandible portions intermediate the distal and proximal ends of said mandible portions.

8. A grasper according to claim 1 further including a sleeve slidably surrounding said shaft, said sleeve having a distal end and a proximal end and being movable between a first retracted position wherein its said distal end is spaced from said pivot portions and a second extended position in which its said distal end forces said pivot portions to exert a force in a direction to cause the proximal ends of said mandible portions to engage one another.

9. A grasper according to claim 1 wherein said pivot portions are coupled to said shaft by a ball joint coupling.

10. A grasper according to claim 9 wherein said ball joint coupling comprises a socket member on the distal end of said shaft and a ball-shaped member connected to said pivot portions.

11. A grasper according to claim 10 wherein said ball-shaped member and said socket member are separable from one another to an extent that allows said jaw assembly to be rotated about the axis of said shaft, and further comprising selectively operable means for pulling said ball-shaped member and said socket member into tight engagement with one another so as to lock said jaw assembly against rotation relative to said shaft.

12. A grasper according to claim 11 wherein said selectively operable means comprises a release/lock cable having a distal end and a proximal end with said distal end connected to said ball member, and further including manually-operable means attached to said proximal end of said release/lock cable for (a) releasing said cable sufficiently to allow said ball-shaped member to rotate relative to said socket member and (b) exerting a pulling force on said release/lock cable so as to lock said ball-shaped member to said socket member.

13. A grasper according to claim 12 wherein said manually-operable means is movably mounted to said body portion of said handle assembly.

14. A grasper according to claim 1 wherein said anchor means is coupled to said handle assembly.

15. A grasper according to claim 1 wherein said jaw assembly is detachable from said handle assembly.

16. A grasper according to claim 15 wherein said anchor means is coupled to said handle assembly.

17. A grasper according to claim 1 wherein said anchor means is located within said shaft and said jaw assembly and said anchor means are detachable from said shaft.

18. A grasper according to claim 17 wherein a portion of said shaft has a side opening through which access may be had to said anchor means, and further including a cover for said side opening.

19. A variable tip-pressure grasping device comprising:

a shaft having a proximal end and a distal end and an internal passageway extending from said proximal end to said distal end;

a jaw assembly positioned at said distal end of said shaft, said jaw assembly comprising first and second jaws with each jaw comprising a mandible section, at least one pivot arm section, and a hinge section interconnecting said mandible section and said at least one pivot arm section, said pivot arm sections extending radially outward from the longitudinal axis of said shaft, said pivot arm sections being pivotally connected to each other and to means coupled to said shaft, and spring means engaged with said mandible sections of said jaws and arranged so as to urge said mandible portions to swing outwardly at said hinge sections;

a sleeve slidably surrounding said shaft, said sleeve having a proximal end and a distal end, said sleeve being movable axially relative to said shaft between a first retracted position wherein its distal end is spaced from said jaw assembly and said jaws are held in a fully open position by said spring means and a second extended position wherein its distal end is engaged with said jaw assembly and forces said jaws toward one another far enough to bring them into a fully closed position in which they are in substantially full face-to-face contact with one another; and actuating means operative when said sleeve is in said first retracted position for moving said first and second jaws from (i) a jaw tip open position in which the distal ends of said jaws have a relatively large gap between them because of the bias exerted by said spring means, to (ii) a first jaw tip closed position in which the distal ends of said jaws are close to one another;

said actuating means comprising first and second actuating cables each having a distal end and a proximal end, with said distal ends connected to said first and second jaws respectively and said proximal ends extending along said internal passageway, and manually operable means connected to the proximal ends of said first and second cables for pulling said cables in a first direction so as to cause said jaws to pivot at said hinge sections so as to move the distal ends of said jaws into said first jaw tip closed position.

20. A device according to claim 19 further including means connected to said actuating cables for locking said cables against movement in a second opposite direction.

21. A device according to claim 19 further including a handle assembly attached to the proximal end of said shaft, and further wherein said actuating means comprises at least one handle member attached to said handle assembly for exerting a pulling force on said actuating cables.

22. A device according to claim 21 further comprising means for locking said at least one handle member in a selected cable-pulling position.

23. A device according to claim 21 wherein said handle assembly comprises a body and said proximal ends of said cables extend into said body, and said actuating means comprises a mechanical linkage between said at least one handle member and said proximal ends of said cables.

24. A device according to claim 19 further including a socket on the proximal end of said shaft, and a cable guide with a ball-shaped section disposed in said socket, said cable guide being disposed between said jaws and slidably engaged with said first and second actuating cables.

25. A device according to claim 24 wherein said handle assembly comprises a body, and further comprising a release cable extending along said internal passageway, said release cable having a distal end attached to said cable guide and a proximal end attached to a release lever attached to said body, said release lever being movable between a cable tight position in which said ball-shaped section is forced into tight engagement with said socket so as to prevent rotational movement of said jaw assembly relative to said shaft and a cable loose position in which said cable is slackened enough to permit said ball shaped section to move relative to said socket, whereby said jaw assembly can be rotated relative to said shaft.

26. A device according to claim 19 further including latch means for locking said sleeve in at least its said retracted position.

27. A device according to claim 20 wherein said latch means comprises a spring biased latch and first and second spaced recesses in said shaft, said recesses being spaced axially along said shaft and being shaped to accommodate a locking portion of said latch whereby to lock said sleeve against axial movement, said recesses being spaced so that one is engaged by said latch when said shaft is in the retracted position and the other is engaged by said latch when said sleeve is in the extended position.

28. A device according to claim 27 wherein said jaw assembly comprises a discrete modular portion of said variable tip-pressure grasping device, said discrete modular portion further comprising means disposed at a proximal portion thereof for releaseably coupling to a hinged portion of said distal end of said shaft thereby providing for attachment and removal of said discrete modular portion.

29. A device according to claim 19 wherein said hinge section of each of said jaws comprises a flexible strip of metal.

30. A device according to claim 19 wherein said spring means engaged With said mandible sections of said jaw assembly comprise three separate springs adapted for outwardly biasing said mandibles and said pivot arm sections.

31. A device according to claim 19 wherein said jaw assembly comprises a second jaw tip closed position in which the distal ends of said jaws engage.

32. A variable tip-pressure grasping device comprising:

a shaft comprising a proximal end portion and a distal end portion, and a internal passageway extending from said proximal end portion to said distal end portion;

first and second actuating cables extending along said passageway, said cables each having a distal end and a proximal end;

a sleeve slidably surrounding said shaft, said sleeve comprising a distal end portion and a proximal end portion and a sleeve handle on said proximal end portion;

a jaw assembly positioned at said distal end of said shaft, said jaw assembly comprising first and second jaws each comprising a mandible having a distal end and a pivot arm interconnected by a flexible hinge, each of said pivot arms extending radially outward from the longitudinal axis of said shaft, said pivot arms being pivotally connected to each other and to said shift, said jaws being biased away from one another by spring means disposed therebetween;

means for pivotally coupling said pivot arms to the distal end of said shaft;

means for connecting said distal ends of said first and second cables to said first and second jaws respectively; and actuating means operative when said sleeve is in said first retracted position for moving said first and second jaws from (i) a jaw tip open position in which said distal ends of said jaws have a relatively large gap between them because of the bias exerted by said spring means, to (ii) a first jaw tip closed position in which said distal ends of said jaws are close to one another.

33. A device according to claim 32 further including a handle assembly attached to said proximal end portion of said shaft, said handle assembly including first and second handle members and said actuating means comprises means connecting said first and second handle members to said first and second cables respectively.

34. A device according to claim 32 wherein said jaw assembly comprises a second jaw tip closed position in which said distal ends of said jaws engage.

* * * * *